United States Patent [19]
Brunner et al.

[11] Patent Number: 5,868,678
[45] Date of Patent: Feb. 9, 1999

[54] TWO-PART MEDICAL PRESSURE TRANSDUCER WITH DIAPHRAGM STAND-OFFS

[75] Inventors: Glenn D. Brunner, Dublin; Charles R. Patzer, Ashville; Nilesh M. Shah, Columbus, all of Ohio

[73] Assignee: Medex, Inc., Hilliard, Ohio

[21] Appl. No.: 759,303

[22] Filed: Dec. 2, 1996

Related U.S. Application Data

[63] Continuation-in-part of Ser. No. 496,080, Jun. 28, 1995, Pat. No. 5,752,918, and Ser. No. 407,903, Mar. 21, 1995, abandoned, which is a division of Ser. No. 85,352, Jun. 30, 1993, Pat. No. 5,417,395.

[51] Int. Cl.$^6$ ........................................................ A61B 5/00
[52] U.S. Cl. ............................ 600/486; 600/488; 600/561
[58] Field of Search ................................... 600/486, 488, 600/561; 73/706, 756

[56] References Cited

U.S. PATENT DOCUMENTS

| | | |
|---|---|---|
| Re. 33,360 | 10/1990 | Reynolds et al. . |
| Re. 33,518 | 1/1991 | McCord et al. . |
| 190,651 | 5/1877 | Webster . |
| D. 283,441 | 4/1986 | Vcelka et al. . |
| D. 302,465 | 7/1989 | Stephens . |
| 344,312 | 6/1886 | Guillemin . |
| 944,312 | 12/1909 | Brede . |
| 1,286,819 | 12/1918 | Snyder . |
| 1,325,902 | 12/1919 | Novick . |
| 2,169,371 | 9/1939 | Payne . |
| 2,371,433 | 3/1945 | Davis . |
| 2,667,184 | 1/1954 | Hailer et al. . |
| 2,762,595 | 9/1956 | Jenne . |
| 3,081,023 | 3/1963 | Taylor . |
| 3,249,105 | 5/1966 | Polanyi . |
| 3,269,550 | 8/1966 | Marcus . |
| 3,429,450 | 2/1969 | Lambert . |
| 3,452,954 | 7/1969 | Lucietto et al. . |
| 3,499,434 | 3/1970 | Ullrich et al. . |
| 3,526,040 | 9/1970 | Young . |
| 3,581,929 | 6/1971 | Guenard . |
| 3,587,322 | 6/1971 | Lebdell et al. . |
| 3,592,187 | 7/1971 | Youdin et al. . |
| 3,599,828 | 8/1971 | Conway et al. . |
| 3,628,526 | 12/1971 | Bigliano . |

(List continued on next page.)

FOREIGN PATENT DOCUMENTS

| | | |
|---|---|---|
| 0077151 | 9/1982 | European Pat. Off. . |
| 0208955 | 6/1986 | European Pat. Off. . |
| 0201207 | 11/1986 | European Pat. Off. . |
| 0247543 | 5/1987 | European Pat. Off. . |
| 1049697 | 1/1952 | France . |
| 1467702 | 2/1966 | France . |
| 2287827 | of 1976 | France . |
| 2619151 | 4/1977 | Germany . |
| 2156081 | 10/1985 | United Kingdom . |
| 2182247 | 5/1987 | United Kingdom . |
| WO8602246 | 4/1986 | WIPO . |
| WO9105576 | 5/1991 | WIPO . |
| WO9207396 | 4/1992 | WIPO . |
| WO9310835 | 6/1993 | WIPO . |
| WO9319318 | 9/1993 | WIPO . |

*Primary Examiner*—Robert L. Nasser
*Attorney, Agent, or Firm*—Wood, Herron & Evans, L.L.P.

[57] ABSTRACT

A medical pressure transducer includes a reusable component with channels to either side of a reusable diaphragm, and a disposable dome with mounting wings to either side of a disposable diaphragm and slidably receivable in the channels to mount the dome with the diaphragms in confronting relationship. Stand-off bumps are provided on the wings which cooperate with support surfaces on the reusable component in the channel to keep the dome and reusable diaphragms sufficiently spaced apart as to minimize deleterious wear thereon when the dome and reusable component are put together and/or taken apart. Dimples may be provided in the support surface to receive the bumps when the diaphragms are in confronting relationship and no longer need to be spaced sufficiently apart. Camming ramps are provided in the channels and on the wings by which to drive the dome diaphragm into the reusable diaphragm.

42 Claims, 3 Drawing Sheets

U.S. PATENT DOCUMENTS

| | | |
|---|---|---|
| 3,631,850 | 1/1972 | Levasseur . |
| 3,646,495 | 2/1972 | Cowmeadow . |
| 3,724,274 | 4/1973 | Millar . |
| 3,818,765 | 6/1974 | Erikse . |
| 3,855,439 | 12/1974 | Hermann. . |
| 3,865,100 | 2/1975 | Kanai et al. . |
| 3,880,151 | 4/1975 | Nilsson et al. . |
| 3,888,559 | 6/1975 | Geib . |
| 3,901,538 | 8/1975 | Blakely . |
| 3,924,881 | 12/1975 | O'Connor . |
| 4,034,612 | 7/1977 | Buckwitz . |
| 4,049,126 | 9/1977 | Halverson . |
| 4,063,553 | 12/1977 | Karsh . |
| 4,064,550 | 12/1977 | Dias et al. . |
| 4,065,970 | 1/1978 | Wilner . |
| 4,072,056 | 2/1978 | Lee . |
| 4,093,076 | 6/1978 | Newton . |
| 4,099,626 | 7/1978 | Magnussen Jr. . |
| 4,108,008 | 8/1978 | Jowett et al. . |
| 4,113,217 | 9/1978 | O'Connell . |
| 4,168,875 | 9/1979 | Leonard, Jr. et al. . |
| 4,182,367 | 1/1980 | Day . |
| 4,185,641 | 1/1980 | Minior et al. . |
| 4,223,921 | 9/1980 | Goyne et al. . |
| 4,226,124 | 10/1980 | Kersten . |
| 4,227,418 | 10/1980 | Bonner et al. . |
| 4,227,420 | 10/1980 | Lamadrid . |
| 4,252,126 | 2/1981 | Mandl . |
| 4,252,131 | 2/1981 | Hon et al. . |
| 4,279,355 | 7/1981 | Schwartz et al. . |
| 4,291,701 | 9/1981 | Bowman . |
| 4,314,480 | 2/1982 | Becker . |
| 4,325,260 | 4/1982 | Takahashi et al. . |
| 4,348,899 | 9/1982 | Muller . |
| 4,365,635 | 12/1982 | Bowman . |
| 4,398,542 | 8/1983 | Cunningham et al. . |
| 4,410,095 | 10/1983 | Dembicks . |
| 4,416,040 | 11/1983 | Towsley . |
| 4,422,794 | 12/1983 | Deken . |
| 4,462,409 | 7/1984 | Pace ........................................ 600/488 |
| 4,491,015 | 1/1985 | Allemano . |
| 4,499,903 | 2/1985 | Furst et al. . |
| 4,505,157 | 3/1985 | Hong Le . |
| 4,524,938 | 6/1985 | Strahs et al. . |
| 4,535,635 | 8/1985 | Claren et al. . |
| 4,539,849 | 9/1985 | Pike . |
| 4,554,927 | 11/1985 | Fussell . |
| 4,562,845 | 1/1986 | Furst et al. . |
| 4,566,597 | 1/1986 | Caputo et al. . |
| 4,574,811 | 3/1986 | Stephens . |
| 4,589,287 | 5/1986 | Dickens . |
| 4,597,291 | 7/1986 | Motomiya . |
| 4,610,256 | 9/1986 | Wallace . |
| 4,611,822 | 9/1986 | Bernhardsen . |
| 4,619,431 | 10/1986 | Matsui . |
| 4,686,764 | 8/1987 | Adams et al. . |
| 4,688,864 | 8/1987 | Sorel . |
| 4,691,573 | 9/1987 | Vamum et al. . |
| 4,717,195 | 1/1988 | Okuyama et al. . |
| 4,732,042 | 3/1988 | Adams . |
| 4,770,297 | 9/1988 | Chang . |
| 4,772,217 | 9/1988 | Petersen . |
| 4,776,343 | 10/1988 | Hubbard et al. . |
| 4,779,625 | 10/1988 | Cole . |
| 4,795,440 | 1/1989 | Young et al. . |
| 4,838,865 | 6/1989 | Flank et al. . |
| 4,856,340 | 8/1989 | Garrison . |
| 4,856,658 | 8/1989 | Novak . |
| 4,881,413 | 11/1989 | Georgi et al. . |
| 4,920,972 | 5/1990 | Frank et al. . |
| 4,944,693 | 7/1990 | Puerner . |
| 4,970,900 | 11/1990 | Shepherd et al. . |
| 4,987,661 | 1/1991 | Kasai . |
| 4,993,265 | 2/1991 | Koen et al. . |
| 5,016,312 | 5/1991 | Frimely . |
| 5,029,478 | 7/1991 | Wamstad . |
| 5,046,625 | 9/1991 | Rushing . |
| 5,112,019 | 5/1992 | Metezler . |
| 5,146,782 | 9/1992 | Rasmussen . |
| 5,155,663 | 10/1992 | Harase . |
| 5,212,989 | 5/1993 | Kodama et al. . |
| 5,218,972 | 6/1993 | Gorsuch et al. . |
| 5,222,946 | 6/1993 | Kamen . |
| 5,257,547 | 11/1993 | Boyer . |
| 5,257,630 | 11/1993 | Broitman et al. . |
| 5,275,367 | 1/1994 | Frye . |
| 5,279,308 | 1/1994 | DiSabito et al. . |
| 5,322,253 | 6/1994 | Stevens . |
| 5,333,507 | 8/1994 | Vogler et al. . |
| 5,351,548 | 10/1994 | Briggs et al. . |
| 5,392,653 | 2/1995 | Zanger et al. . |
| 5,404,756 | 4/1995 | Briggs et al. . |
| 5,406,952 | 4/1995 | Barnes et al. . |
| 5,410,916 | 5/1995 | Cook . |
| 5,417,395 | 5/1995 | Fowler et al. . |
| 5,551,300 | 9/1996 | Vurek et al. . |
| 5,554,113 | 9/1996 | Novak et al. . |

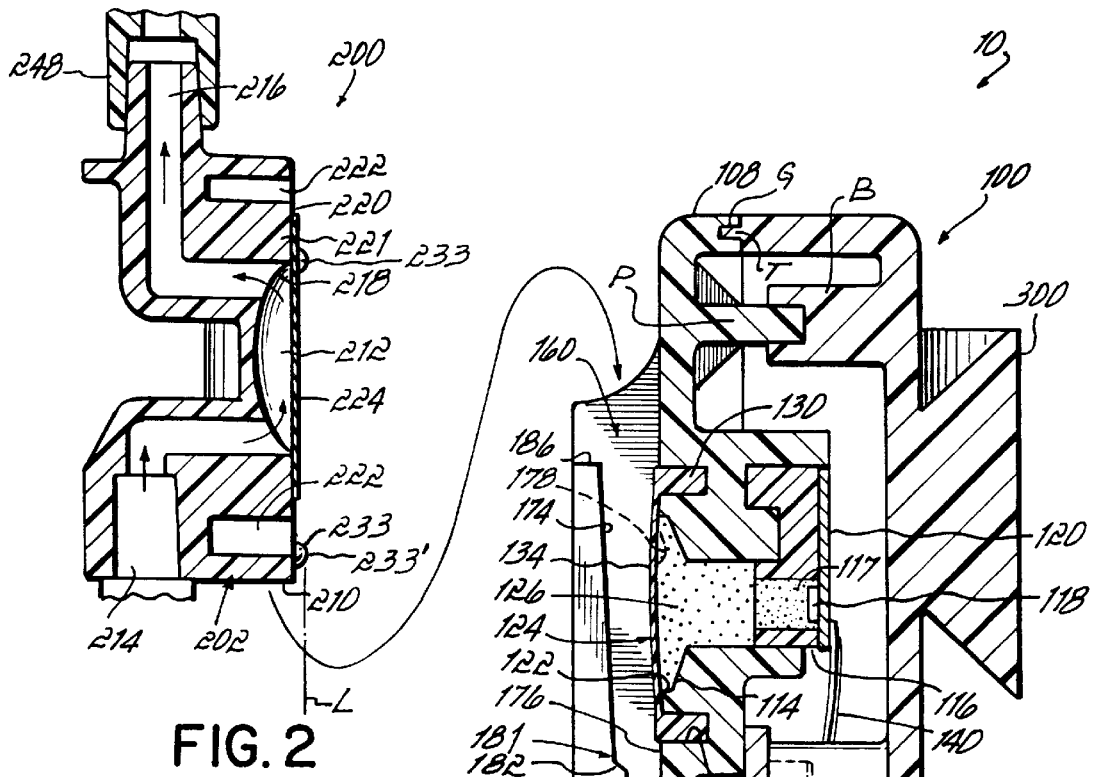
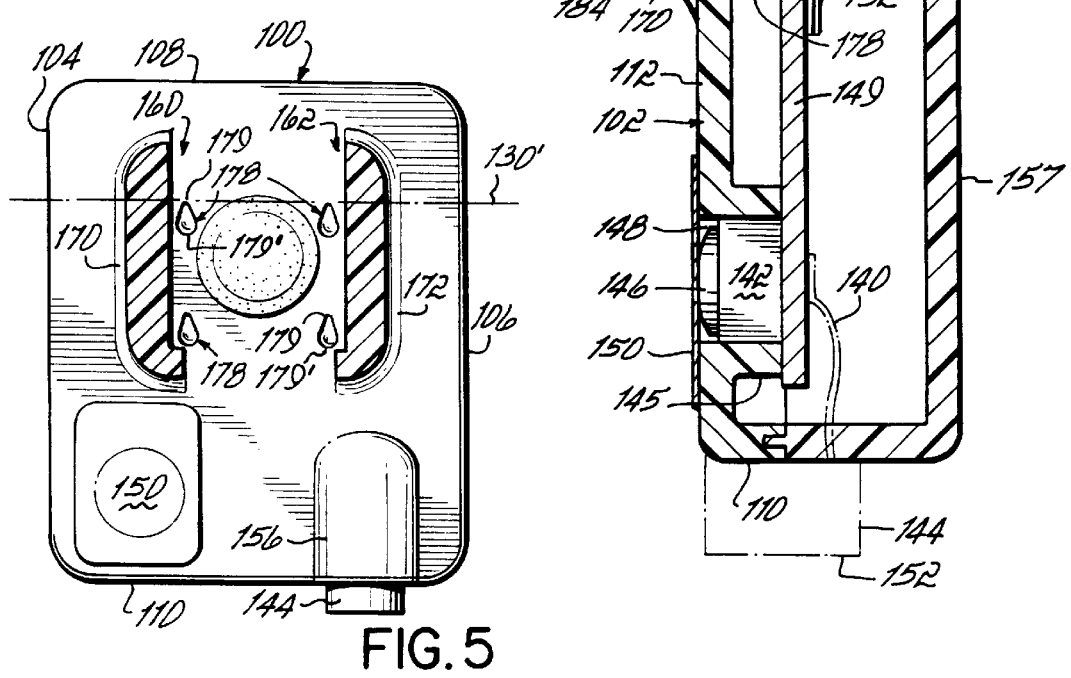
FIG. 2
FIG. 5

TWO-PART MEDICAL PRESSURE TRANSDUCER WITH DIAPHRAGM STAND-OFFS

RELATED APPLICATIONS

This application is a continuation-in-part of applications Ser. No. 08/496,080, filed Jun. 28, 1995, entitled Modular Medical Pressure Transducer, now U.S. Pat. No. 5,472,918 and Ser. No. 08/407,903, filed Mar. 21, 1995, now abandoned entitled Modular Interconnecting Component Support Plate, the latter of which is a divisional of application Ser. No. 08/085,352, filed Jun. 30, 1993, now U.S. Pat. No. 5,417,395. The disclosures of aforementioned applications Ser. Nos. 08/496,080, 08/407,903 and 08/085,352 are incorporated herein by reference in their entirety.

BACKGROUND OF THE INVENTION

I. Field of the Invention

This invention relates to medical pressure transducers and, more particularly, to such transducers in which a disposable fluid path component such as a dome is selectively attachable to a reusable sensor component with respective fluid pressure communicating diaphragms of the components in confronting, pressure communicating relationship.

II. Description of Prior Art

In hospital environments, for example, many procedures involve monitoring bodily fluid pressures such as blood pressure. Typically, such pressure is monitored with a medical pressure transducer outside the patient's body and coupled hydraulically to the patient's circulatory system, by way of example, via a catheter introduced into the body. The catheter is coupled via a tube to a fluid path inside the transducer and the tube is filled with saline to hydraulically communicate pressure within the patient's body to the transducer.

The transducer includes a sensor in pressure communication with the fluid path by which to convert the pressure therein to electrical signals corresponding to the pressure. The electrical signals are coupled via a cable to a monitor which provides a visual display of the pressure.

One particularly successful form of such a transducer is provided by a two-component system in which one component with the expensive sensor is reusable, and the other component with the patient-contacting fluid path is disposable. Each component is provided with a diaphragm closing off access to the sensor or the fluid path, respectively. To measure pressure in the fluid path, the disposable component is screwed onto the reusable component with the diaphragms in confronting, pressure communicating relationship to thereby communicate pressure from the fluid path to the sensor. After use, the disposable component is unscrewed from the reusable part and discarded, and replaced with a new, sterile unit.

U.S. Pat. No. 4,920,972, the disclosure of which is incorporated herein by reference, shows an example of a two-component transducer in which the disposable fluid path component, referred to as a fluid dome, is rotatably coupled to the reusable sensor portion. The components are secured together by threaded interaction to bring the diaphragms into confronting, pressure communication relationship by relative rotation between the dome and reusable component and the diaphragms thereof.

While there has been success with such screw-on types of transducers they can be difficult to manipulate and can present other impediments to their use. For example, the diaphragms tend to rub together over a significant part of the rotational travel of the dome and reusable component. This rubbing causes a wearing effect on the diaphragms, and especially the reusable diaphragm which must remain intact for multiple uses. The wearing of the reusable diaphragm is thus of particular concern as there can be a noticeable shortening in the useful life of the reusable component and its performance may be adversely affected as the wear becomes pronounced.

SUMMARY OF THE INVENTION

The present invention provides a simple-to-use two-component type of system in which wear on the reusable diaphragm is substantially reduced, if not eliminated, so as to prolong the useful life of the reusable component. To this end, and in accordance with the principles of the present invention, the two components are designed to be slid together by translation along a generally straight line, rather than by relative rotation, and further include stand-off structure to keep the dome and reusable diaphragms sufficiently apart that they do not deleteriously rub together over most of the extent of travel between the components. In accordance with one aspect of the present invention, the dome is provided with at least one mounting wing, and advantageously a pair of such wings disposed to different sides of the dome diaphragm, and the reusable component is provided with a channel member, and advantageously a pair of channel members to different sides of the reusable diaphragm, with the wings and channel members being configured to slidably engage together generally along a straight line without relative rotation between the dome and the reusable component whereby to bring the diaphragms into substantially full confronting relationship.

In accordance with a further aspect of the present invention, the dome wings are each provided with stand-off projections to maintain the separation between the diaphragms until the dome is fully inserted into the reusable component whereat the diaphragms are permitted to fully contact one another. The wing projections may be bumps on the underside of the wings which have distal ends extending at least to, and advantageously beyond, the plane of the dome diaphragm. The reusable component may be provided with a support surface that cooperates with the dome bumps to help maintain sufficient separation to avoid deleterious wear of the diaphragms as the dome slides into the reusable component. Dimple recesses may optionally be provided in the support surface to receive the distal ends of the wing projections at the end of the dome travel when the diaphragms are to be in full contact. Advantageously, the recesses are tear-drop shaped. Further, the dome wings and/or channel members may be provided with camming structure by which to drive the disposable diaphragm into the reusable diaphragm as the dome nears the end of its sliding travel into the reusable component. Provision of the camming structure allows the two diaphragms to initially be slightly spaced apart, or loosely contacting, through at least a significant part of the travel of the dome into the reusable component. In this way, the diaphragms are not significantly damaged or chafed as they slide by one another. Yet, the camming structure brings the diaphragms into abutting relationship, at least at the end of the travel of the components, such that proper pressure communication is established therebetween.

By virtue of the foregoing, there are thus provided two, easy-to-use components making up a medical pressure transducer system both of which are designed to minimize deleterious abrasion and wear on the diaphragms thereof, and especially the diaphragm of the reusable component.

These and other objects and advantages of the present invention shall become apparent from the accompanying drawings and the detailed descriptions thereof.

BRIEF DESCRIPTION OF THE DRAWINGS

The accompanying drawings, which are incorporated in and constitute a part of this specification, illustrate an embodiment of the invention and, together with a general description of the invention given above, and the detailed description given below, serve to explain the principles of the invention.

FIG. 2 is an exploded, cross-sectional view taken along lines 2—2 of FIG. 1;

FIG. 5 is a front plan view of the reusable component of FIG. 1 with the channel walls removed.

DETAILED DESCRIPTION OF THE DRAWINGS

Figure 1:
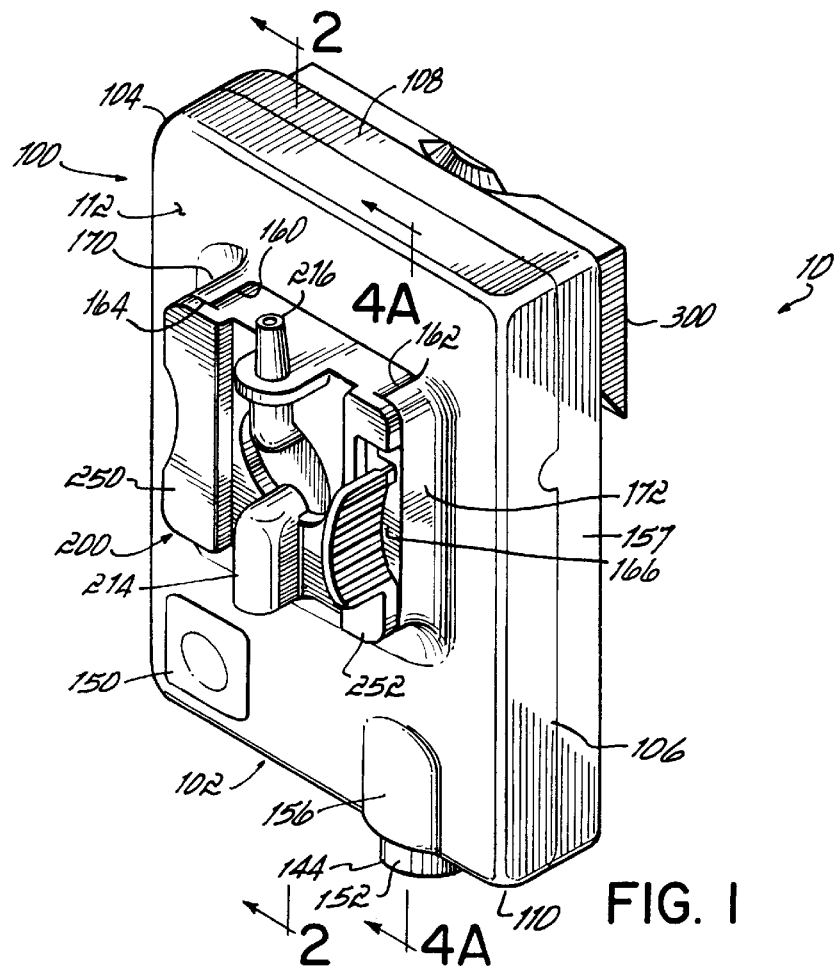
FIG. 1 is a perspective view of an embodiment of a transducer of the invention.

With reference to FIG. 1, there is shown a perspective view of a medical pressure transducer 10 of the present invention. Transducer 10 includes two major components, one being a reusable sensor component 100 of the invention and the other being a disposable fluid dome component 200 of the invention, removably and slidably mounted to reusable component 100.

With further reference to FIGS. 1 and 2, reusable component 100 is a pole-mountable supporting plate or housing with a reusable pressure sensor system built into it as will be described. To this end, component 100 may be seen as having an opaque plastic support 102 in the form of a plate. Plate 102 has generally planar left edge 104, generally planar right edge 106, and generally planar top and bottom edges 108,110 to define a generally rectangular shape to plate 102. Extending between edges 104, 106, 108, 110 is a generally planar front face 112.

Extending from behind face 112 is an integral sensor chamber 114. Permanently attached within sensor chamber 114, such as by adhesive (not shown), is a plastic chimney 116 filled with cured gel 117 at the bottom of which is an integrated circuit sensor chip 118 mounted to printed circuit (PC) board substrate 120 with a small vent hole (not shown) therethrough to vent chip 118. PC board 120 contains appropriate circuitry thereon (not shown) and is affixed with chimney 116 to thus permanently associate sensor 118 with reusable component 100. At the upper end of chamber 114 through face 112 is an aperture 122. Permanently mounted over aperture 122 is an elastomeric reusable diaphragm 124 such as of molded polyurethane. Additional gel 126 is inserted in liquid state into chamber 114 between diaphragm 124 and chimney 116 via a fill port (not shown) to bring diaphragm 124 into pressure communication, via gels 126 and 117, with sensor 118. The fill port is sealed such as by insertion of a tightly-fitting ball or screw or the like (not shown) to thus slightly distend diaphragm 124 and gel 126 is cured.

The edge 130 of diaphragm 124 defines a cylindrical collar that is fitted into annular groove 132 in face 112 about aperture 122 to hold diaphragm 124 to support 102 with the front face or surface 134 of reusable diaphragm 124 exposed in, or bulging just slightly above, the plane of front face 112. A plurality of conductors 140 interconnect calibration test switch 142 and connector 144 to PC board substrate 120 circuitry and sensor 118, all behind face 112 of plate 102. Switch 142 is fitted within open-bottom well 145 formed into face 112 with switch button 146 being accessible at aperture 148 through plate face 112 in the lower left corner thereof as seen from the front. Conductors 140 could be separate wires or ribbon cable and/or conductive traces (not shown) on a switch-supporting PC board 149. Placed over aperture 148 is a compliant, polycarbonate membrane 150 to protect switch 142 and to allow actuation thereof such as by gripping of reusable component 100 between the thumb and forefinger (not shown) in the area of membrane 150 and compressing same. Membrane 150 is adhesively held along its perimeter to the edge of well 145 defined at aperture 148. Actuation of switch 142 provides a calibration test as generally described in U.S. Pat. No. 4,760,730, the disclosure of which is incorporated herein by reference, but as a directly integral part of the reusable component, rather than as a separate component.

To electrically connect to a monitor (not shown), connector 144 is provided at the bottom right of component 100 as seen from the front. Connector 144 may have a cylindrical plastic shell 152 with female pin-receiving connectors (not shown) therein and housed in a bulbously protruded area 156 of component 100. Connector 144 may form part of a two-connector set as shown in U.S. Pat. No. 5,167,522. An opaque plastic back plate 157 may be secured, such as by adhesive (not shown), over the back side of plate 102 to enclose the above-mentioned components, with a tongue T and groove G arrangement between their connecting sides to thus define a complete housing. Alternatively, plate 157 may be press-fit to plate 102 by interaction of the tongue T and groove G and pins P and bosses B. Also, the housing defined by plate 102 and back 157 may be vented, such as via a small through-hole or path (not shown) formed through mount 300. A filter member (also not shown) may be included with the through-hole or path. Additionally, plate 157 is adapted to be mountable to a pole and thus includes mount 300 to connect to a pole-mount as shown in aforesaid U.S. patent application Ser. No. 08/496,080.

To mount disposable dome component 200 to reusable sensor housing 100 as will be described, plate 102 is provided with channel members which are defined by a pair of channels 160,162 disposed to opposite left and right sides of reusable diaphragm 124 as seen from the front. Each channel 160,162 is defined behind a respective outer front wall 164,166 associated with plate 102. To this end, outer front walls 164,166 are generally parallel to, but spaced from, front face 112 and held thereto by interconnecting side walls 170,172, respectively, to thus define channels 160,162 between front face 112 and the underside 174 of each respective outer front wall 164,166. The lateral extent of each channel 160,162 is further defined by side walls 170,172, respectively.

The underside 174 of outer front wall 164 or 166 may be slightly angled with a draft (such as for molding) as it progresses from near the top edge 108 of plate 102 towards the bottom edge 110 thereof. The draft narrows somewhat the width of the channel 160 or 162 in the direction of insertion travel of the dome 200. For purposes described hereinafter, surface 176 of face 112 within each channel 160,162 defines a support surface and may include dimple recesses 178. As best seen in FIG. 5, the upper pair of recesses 178 are positioned so that the tops 179 intersect a line tangent to top edge 130' of diaphragm 124, with the lower or bulbous portion 179' of recesses extending therebelow. Similarly, the lower pair of recesses 178 are spaced near the terminal or bottom end 180 of the channels 160, 162 and below the diaphragm 124. Advantageously, dimples 178 are tear-drop shaped with the tops 179 sloping up to the surface 176 as seen in FIG. 2. Also, camming structure is provided at the terminal or bottom end 180 of the channels 160,162. The camming structure in the embodiment shown is provided by camming ramp 181 comprised of a 45° ramp 182 and a trailing step 184 to define a generally precise channel width $W_c$ thereat (see FIG. 4A). The top edge 186 of each wall 164,166 is exposed. The bottom end 180 of each channel 160 or 162 may be closed off or left open as desired.

Figure 3:
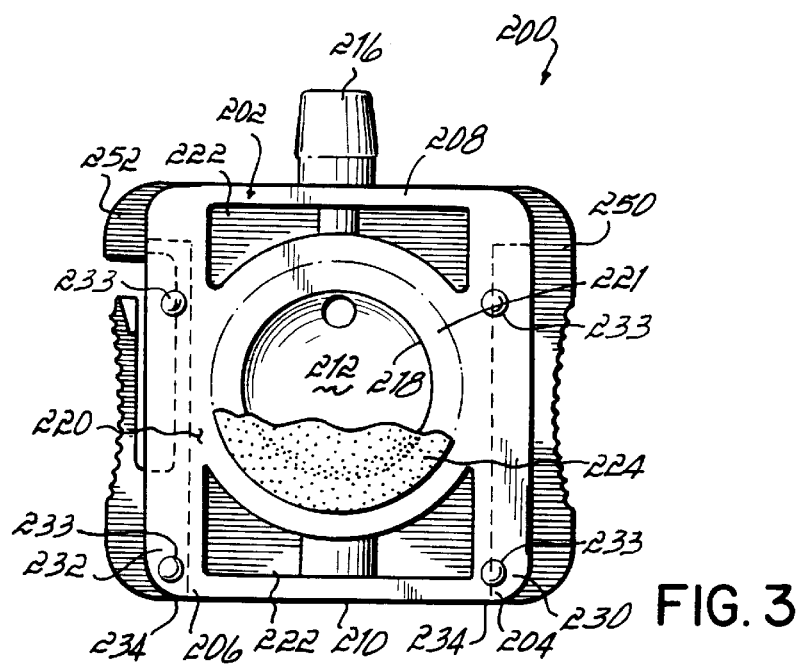
FIG. 3 is a rear, partially cut-away view of the disposable component of FIG. 1.

With particular further reference to FIGS. 2 and 3, disposable dome 200 is of clear or translucent plastic and may be seen as having a central body portion 202 defined between left and right edges 204,206 and top and bottom edges 208, 210 to define a generally rectangular shape to central body portion 202. Formed centrally through the back of body portion 202 is a fluid path well 212 which communicates through an inlet port 214 extending up out of the front of well 212 and accessible along bottom edge 210 and outlet pipe 216 extending up out of the front of well 212 and beyond top edge 208. Inlet and outlet 214 and 216 cooperate to extend fluid path 212 through disposable dome 200. Fluid path 212 is accessible through a large aperture 218 along the back side 220 of central portion 202. Well 212 and aperture 218 are defined by a cylindrical wall 221 in central portion 202 with cavities 222 defined between wall 221 and edges 204,206,208,210. Alternatively, cavities 222 could be filled with plastic. Either way, back side 220 of dome 200 functions to define a flat or plate-like surface to dome 200 to match up to planar face 112 of plate 102.

Extending across aperture 218 along bottom side 220 is an elastomeric diaphragm 224 permanently affixed to central portion 202 and providing a pressure transmitting, fluid impervious wall to seal the fluid path within dome 200. Diaphragm 224 could be a molded polyurethane, like diaphragm 124 with a collar (not shown) mounted within an annular recess or groove (also not shown) about aperture 218. Alternatively, diaphragm 224 could be a sheet of urethane film material, the peripheral edge of which is either adhesively or thermally bonded to the edge of aperture 218, or is held into a groove (not shown) about aperture 218 such as by a compression ring (also not shown).

To mount dome 200 to reusable component 100, the dome is provided with a pair of edges that translationally rather than rotationally mate with the channel members 160, 162 of the reusable component 100. To this end, extending outwardly from opposite left and right sides of central portion 202 (from edges 204 and 206, respectively) and to either side of diaphragm 224 are left and right mounting wings 230,232 situated to be matingly received within channels 160,162 of reusable plate 102 in a translational or sliding and non-rotational manner such as to place disposable diaphragm 224 into substantially full confronting relationship with reusable diaphragm 124.

A pair of projecting bumps 233 are carried on the underside of each wing 230,232. Distal tips 233' of bumps 233 project at least to, and advantageously beyond, a plane L defined by diaphragm 224 of dome 200 as seen in FIG. 2 (which shows bumps 233 greatly exaggerated for ease of viewing). The upper pair of bumps 233 near the top edge 208 of dome 200 are positioned slightly below a line tangent to the uppermost edge of dome diaphragm 224. The lower pair of bumps 233 are spaced near bottom edge 210 such that bumps 233 mate into respective dimples 178 of component 100 when dome 200 is seated therein. Bottom end 234 of each wing 230,232 is chamfered as at 235 (see FIG. 4A) for purposes to be described hereinafter. Bottom end 234 just above chamfer 235 has a generally precise thickness or width, which in combination with diaphragms 224 and 124, is closely equal to channel width $W_c$ so as to hold the diaphragms in proper pressure communicating relationship. Further camming structure is defined at top or distal end 236 of each wing. In the embodiment shown, the further camming structure is provided by camming ramp 240 which, like the camming ramp 181 within channels 160 and 162, is comprised of a 45° ramp 242 and a trailing step 244 to define a precise width $W_w$ of wing 230 or 232 in the area of trailing step 244. In this regard, the thickness or width of the channels 160,162 at their openings near the top edge 108 of plate 102 cooperate with diaphragms 224 and 124 to closely equal width $W_w$ so as to, in addition or alternatively to the holding ability of bottom end 234 and width $W_c$, hold the diaphragms in proper pressure communicating relationship.

Bumps 233 are provided to help maintain sufficient spacing between diaphragm 224 and diaphragm 124 as dome 200 is slid into reusable component 100 by which to avoid deleterious wear of the diaphragms. To this end, the sufficient spacing may allow for loose contact between the diaphragms it being understood that some contact may be unavoidable. To further enhance the useful life of the reusable diaphragm 124, the dome diaphragm 224 may be provided with a lubricant or surface coating (neither shown) such as medical grade silicone oil to minimize damage even in the cases of some contact between the diaphragms and as they are brought fully together when in substantially full confronting relationship. In this manner, as the dome 200 travels into reusable component 100, there may be a slight space (or just loose, sliding contact) between the diaphragms 124 and 224 so as not to harmfully abrade at least diaphragm 124.

As dome 200 nears the end of its longitudinal travel into reusable component 100, the camming structure may come into play. To this end, camming ramp 181 and camming ramp 240 are situated on respective ones of the reusable component 100 and disposable dome 200 so as to engage their respective counterpart structures near the tailing end of the travel of dome 200 as the wings 230,232 are slidably received into the channels 160,162 of the reusable component 100. More specifically, as dome diaphragm 224 comes into substantially full confronting relationship with reusable diaphragm 124, wings 230,232 are driven, in a somewhat axial direction, towards face 112 and diaphragm 124 of plate 102 such that disposable diaphragm 224 is driven into abutting relationship with reusable diaphragm 124 to provide a proper pressure communicating relationship therebetween. When in that position, bumps 233 fit into the large aspect 179' of optional teardrop dimples 178 having slid into the teardrop tips 179' on final seating of dome 200 as will be readily appreciated. Consequently, dimples 178 further facilitate full contact between the diaphragms, although it will be readily apparent to one skilled in the art that dimples 178 may be dispensed with (in which event bumps 233 should extend only to about plane L).

To limit the extent of travel of dome 200 relative to plate 102, a closing wall 246 may be provided at distal or top end 236 of each wing 230,232 which closing wall 246 will abut into top edge 186 of outer front walls 164 or 166. An additional or secondary wing 250 and/or locking tab structure 252 may be provided as more specifically described in aforesaid U.S. patent application Ser. No. 08/496,080. Also, dome 200 may be provided with a fast-flush device (not shown) coupled to inlet port 214 (such as the fast flush device shown in U.S. Pat. No. 5,171,230) and a stopcock 248 coupled to outlet pipe 216. The flush device may then be connected by tubing to a source of saline (not shown) and the stopcock may be connected by further tubing to a catheter (not shown) to be placed within the patient's circulatory system (not shown) to thus monitor the pressure thereof as in the case of sensor 102 in FIG. 7 of U.S. Pat. No. 5,221,271, the disclosure of which is incorporated herein by reference. While the use of two wings and two channels is shown in the embodiment described, at least only one of each may be employed. Also, the outer front walls may be coplanar with front face 112 with appropriate adjustment in the elevation of either diaphragm 124 or mounting wings 230,232, by way of example.

Figure 4C:
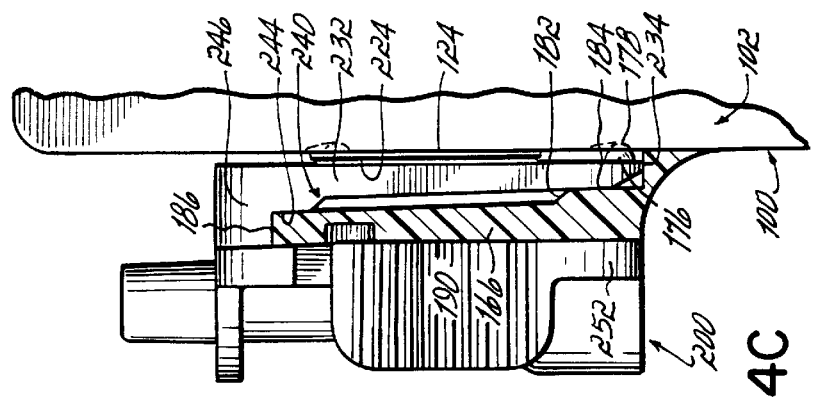
FIGS. 4A–4C are diagrammatic side views, taken along lines 4A—4A of FIG. 1, to illustrate interaction of the dome wings and reusable component channels.
Figure 4B:
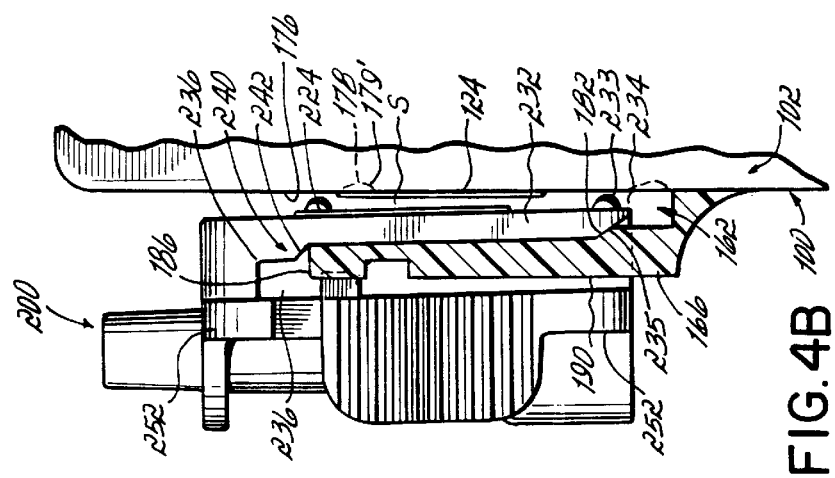
Figure 4A:
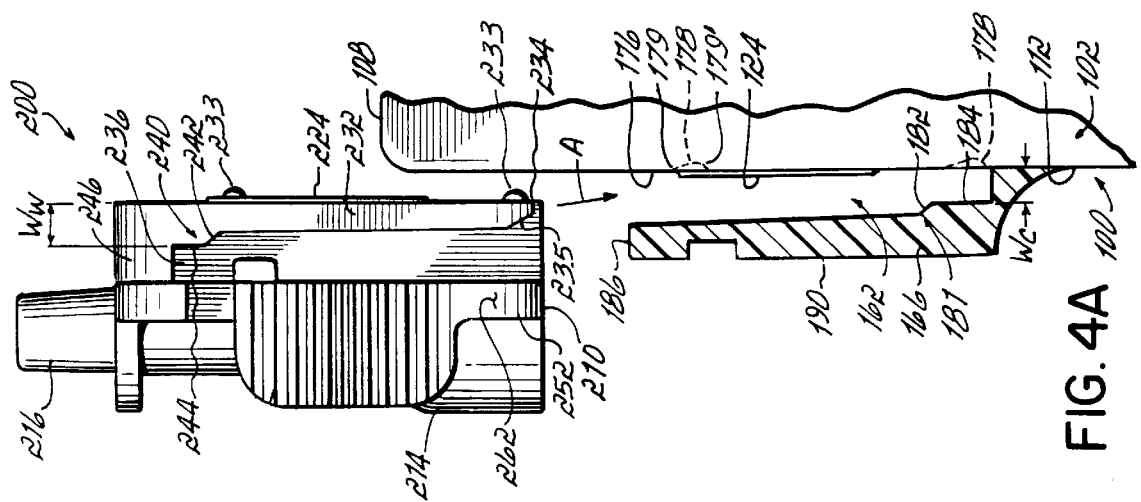

With reference to FIGS. 4A–4C (in which channel 160 and its associated walls are removed for sake of clarity), there is shown diagrammatically the mounting of dome 200 to reusable component 100 in accordance with the various aspects of the present invention. In FIG. 4A, the diaphragms are spaced well apart and dome 200 is just about to be mounted to plate 102 with wing 232 just beginning to enter channel 162 in a direction along the downwardly-directed arrow A. Thus, dome wing 232 is coming into channel 162 from the direction of top edge 108 of plate 102. Top end 186 of outer front wall 166 may be impacted by chamfered wall 235 at the proximal end of wing 232 to help force wing 232 into the space or channel 162 defined behind outer front wall 166. In FIG. 4A, second wing 252 is spaced above and away from top surface 190 of front wall 166.

Dome 200 continues in its downward progression towards bottom wall 110 along a generally straight line without substantial rotation between the dome and the reusable component as indicated in FIG. 4B. As the translation of the dome in to the reusable component thus continues, most of the length of wing 232 passes into channel 162. In this progression of travel, it may be seen that bumps 233 may bear against support surface 176 so as to maintain sufficient spacing (i.e., a slight space or at least a loose or sliding contact all as indicated by the letter S) between diaphragms 224 and 124 so as to avoid damaging or chafing the diaphragms, and especially diaphragm 124 which is intended to be reusable with several of domes 200. Near the end of the travel, as the diaphragms are brought into substantially full confronting relationship, chamfer 235 hits against ramp 182 of camming ramp 181 to start to drive the proximal end of wing 232 towards face 112 and diaphragm 124. At about the same time, camming ramp 240 impacts against top edge 186 to also drive the distal end of wing 232 towards face 112 and diaphragm 124 in which event the spacing S between diaphragms 224 and 124 begins to decrease (or the loose contact begins to tighten up).

In the end of the travel of dome 200 into reusable component 100 in FIG. 4C with the diaphragms in substantially full confronting relationship, the proximal end of wing 232 is situated below and against trailing end 184 and the top end 186 of outer wall 166 is situated above and against trailing end 244 of wing camming ramp 240 such that wing 232 has been driven towards plate face 112, bumps 233 have dropped into dimples 178 (if present), and diaphragms 224 and 124 have been driven into abutting relationship to provide the desired pressure communicating relationship therebetween. The same arrangement of travel as shown in FIGS. 4A–4C occurs simultaneously between wing 230 and channel 160.

In use, dome 200 is slidably mounted to reusable component 100 as above described and appropriate tubing and a catheter are employed to couple fluid path 212 of transducer 10 to a patient and connector 144 utilized to couple signals representing the patient's blood pressure, for example, with a monitor in an otherwise conventional manner such as FIG. 6 of the aforementioned U.S. Pat. No. 5,221,271. After the use for that patient is completed, or should dome 200 need to be replaced for any reason, dome 200 may be removed by sliding dome 200 out of channels 160,162 of reusable component 100 and the dome 200 disposed of (with or without tubing). Either new tubing may be provided, or the old tubing used, with a new dome 200 as appropriate, depending upon the patient's situation, and new dome 200 slidably remounted to reusable component 100 as previously described.

By virtue of the foregoing, there are thus provided the two components of a medical pressure transducer in which the disposable dome and the reusable component are designed to mate together in a simple and easy manner by relative sliding rather than rotation and with little or no deleterious abrasion of the diaphragms.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the wing(s) and channel(s) are shown as being disposed to opposite sides of their respective diaphragms, they need not be so positioned. Similarly, the projections may be placed on the reusable component with the support surface and optional dimples being provided on the dome. The invention in its broader aspects is therefore not limited to the specific details, representative apparatus and method and illustrative example shown and described. Accordingly, departures may be made from such details without departing from the scope or spirit of applicant's general inventive concept.

What is claimed is:

1. A medical pressure transducer disposable dome for use with a reusable component having a pressure sensor and diaphragm in pressure communication with said sensor and having at least one channel member disposed to one side of said reusable component diaphragm, the disposable dome comprising:

a fluid path adapted to be coupled to a patient;

a diaphragm coupled to the fluid path; and at least one mounting wing having a free end disposed to extend laterally outwardly from the dome to one side of the dome diaphragm and being configured to slidably engage into said reusable component channel without substantial rotation of the dome relative to said reusable component wherein to bring the dome diaphragm into confronting relationship with said reusable component diaphragm upon sliding the dome wing into said channel, the disposable dome further comprising stand-off means associated with the dome wing for maintaining sufficient separation between the dome diaphragm and said reusable component diaphragm as the dome wing is slid into said channel.

2. The disposable dome of claim 1, the stand-off means including a projection having a distal end extending to at least a plane defined by the dome diaphragm.

3. The disposable dome of claim 2, wherein the distal end of the projection extends beyond the dome diaphragm plane.

4. The disposable dome of claim 1, the stand-off means including a bump carried on an underside of the mounting wing.

5. The disposable dome of claim 1, the stand-off means including a pair of spaced-apart projections each having a distal end extending to at least a plane defined by the dome diaphragm.

6. The disposable dome of claim 5, wherein the distal ends of the projections extend beyond the dome diaphragm.

7. The disposable dome of claim 1, the stand-off means including a pair of spaced-apart bumps carried on an underside of the mounting wing.

8. The disposable dome of claim 1 further comprising a second mounting wing disposed to an opposite side of the dome diaphragm and second stand-off means associated with the second dome wing for maintaining said sufficient separation.

9. A medical pressure transducer disposable dome comprising:
    a fluid path adapted to be coupled to a patient;
    a diaphragm coupled to the fluid path;
    a pair of mounting wings extending laterally outwardly from the dome to opposite sides of the diaphragm; and
    a plurality of spacing bumps carried on the undersides of the mounting wings.

10. The transducer of claim 9 wherein each mounting wing carries two of the bumps, the bumps on each mounting wing being spaced apart along the associated wing.

11. A medical pressure transducer disposable dome for use with a reusable component having a pressure sensor and diaphragm in pressure communication with said sensor and having at least one channel member, the disposable dome comprising:
    a fluid path adapted to be coupled to a patient;
    a diaphragm coupled to the fluid path; and
    at least one mounting wing having a free end extending laterally outwardly from the dome and being configured to slidably engage into said reusable component channel wherein to bring the dome diaphragm into confronting relationship with said reusable component diaphragm upon sliding the dome wing into said channel, the disposable dome further comprising a rigid projection situated to maintain separation between the dome diaphragm and said reusable component diaphragm as the dome wing is slid into said channel.

12. The disposable dome of claim 11, the projection being rigidly connected to the mounting wing.

13. A medical pressure transducer disposable dome for use with a reusable component having a pressure sensor and diaphragm in pressure communication with said sensor and having at least one channel member, the disposable dome comprising:
    a fluid path adapted to be coupled to a patient;
    a diaphragm coupled to the fluid path; and
    at least one mounting wing being configured to slidably engage into said reusable component channel whereby to bring the dome diaphragm into confronting relationship with said reusable component diaphragm upon sliding the dome wing into said channel, the disposable dome further comprising a rigid projection situated to maintain separation between the dome diaphragm and said reusable component diaphragm as the dome wing is slid into said channel, the mounting wing and projection extending in perpendicular directions relative one another.

14. A medical pressure transducer comprising:
    a reusable component having a pressure sensor and a diaphragm in pressure communication with the sensor, the reusable component further having at least one channel member; and
    a disposable dome having a fluid path adapted to be coupled to a patient, a diaphragm coupled to the fluid path, and at least one mounting wing, the mounting wing and channel member being configured to slidably engage together without relative rotation between the dome and the reusable component wherein to bring the dome diaphragm into confronting relationship with the reusable component diaphragm upon sliding the dome wing into the channel, the disposable dome further comprising stand-off means associated with the dome wing for maintaining separation between the dome diaphragm and the reusable component diaphragm as the dome wing is slid into the channel.

15. The transducer of claim 14, the disposable dome stand-off means including a projection having a distal end extending to at least a plane defined by the dome diaphragm.

16. The transducer of claim 15, wherein the distal end of the projection extends beyond the dome diaphragm plane.

17. The transducer of claim 14, the disposable dome stand-off means including a bump carried on an underside of the mounting wing.

18. The transducer of claim 14, the disposable dome stand-off means including a pair of spaced-apart projections each having a distal end extending to at least a plane defined by the dome diaphragm.

19. The transducer of claim 18, wherein the distal ends of the projections extend beyond the dome diaphragm plane.

20. The transducer of claim 14, the stand-off means including a pair of spaced apart bumps carried on an underside of the mounting wing.

21. The transducer of claim 14, the channel being disposed to one side of the reusable component diaphragm and the mounting wing being disposed to one side of the dome diaphragm.

22. A medical pressure transducer comprising:
    a reusable component having a pressure sensor and a diaphragm in pressure communication with the sensor, the reusable component further having at least one channel member; and
    a disposable dome component having a fluid path adapted to be coupled to a patient, a diaphragm coupled to the fluid path, and at least one mounting wing, the mounting wing and channel member being configured to slidably engage together without relative rotation between the dome and the reusable components wherein to bring the dome diaphragm into confronting relationship with the reusable component diaphragm upon sliding the dome wing into the channel;
    the reusable component and disposable dome component including cooperating means for maintaining separation between the dome diaphragm and the reusable component diaphragm as the dome wing is slid into the channel and for situating the dome diaphragm against the reusable component diaphragm as the diaphragms are slid into confronting relationship.

23. The transducer of claim 22, wherein the cooperating means includes (i) a projection associated with one of the components; and (ii) a support surface of the other one of the components.

24. The transducer of claim 23, the cooperating means further including recess means associated with the component having the support surface for receiving the projection as the diaphragms are slid into confronting relationship.

25. The transducer of claim 24, the recess means being defined in the support surface.

26. The transducer of claim 24, wherein the recess means is defined by a teardrop-shaped dimple.

27. The transducer of claim 23 wherein the projection is carried on an underside of the disposable dome component mounting wing and the support surface is defined within the channel of the reusable component.

28. The transducer of claim 27, the cooperating means further including recess means within the channel for receiving the projection as the diaphragms are slid into confronting relationship.

29. The transducer of claim 28, the recess means being defined in the support surface.

30. The transducer of claim 28 wherein the recess means is defined by a teardrop-shaped dimple.

31. The transducer of claim 23 wherein the cooperating means includes a bump carried on an underside of the dome component mounting wing and a support surface of the reusable component within the channel.

32. The transducer of claim 23, the cooperating means further including recess means within the channel for receiving the bump as the diaphragms are slid into confronting relationship.

33. The transducer of claim 32 wherein the recess means defines a dimple.

34. The transducer of claim 33, the recess means being defined in the support surface.

35. The transducer of claim 33, the dimple being teardrop-shaped.

36. The transducer of claim 22, the channel being disposed to one side of the reusable component diaphragm and the mounting wing being disposed to one side of the dome diaphragm.

37. A reusable medical pressure transducer component having a pressure sensor and a diaphragm in pressure communication with the sensor, the reusable component further having at least one channel member disposed to one side of the reusable component diaphragm and recess means for receiving a stand-off projection of a disposable dome when a diaphragm of said dome is in confronting relationship to the reusable component diaphragm.

38. The reusable component of claim 37, the recess means defining a dimple.

39. The reusable component of claim 38, the dimple being teardrop-shaped.

40. The reusable component of claim 37, further comprising a second channel member disposed to an opposite side of the reusable component diaphragm and second recess means for receiving a second stand-off projection of said disposable dome.

41. A method of mounting a disposable dome to a reusable sensor wherein the dome includes a fluid path adapted to be coupled to a patient and a diaphragm coupled to the fluid path and the reusable sensor includes a diaphragm in pressure communication therewith, the method comprising:

with the diaphragms spaced apart, sliding the dome and sensor relative to one another along a generally straight line from a position where the diaphragms are not in confronting relationship towards a substantially full confronting relationship;

continuing to slide the dome and sensor relative to one another along the generally straight line so as to bring the diaphragms into substantially full confronting relationship; and causing the diaphragms to be in contact with one another when in the substantially full confronting relationship.

42. The method of claim 41 wherein the diaphragms are caused to come into contact with one another as they are brought into the substantially fully confronting relationship.

* * * * *